United States Patent
Oida et al.

(10) Patent No.: US 11,914,012 B2
(45) Date of Patent: Feb. 27, 2024

(54) BRAIN MEASUREMENT APPARATUS AND BRAIN MEASUREMENT METHOD

(71) Applicants: HAMAMATSU PHOTONICS K.K., Hamamatsu (JP); Kyoto University, Kyoto (JP)

(72) Inventors: Takenori Oida, Hamamatsu (JP); Takahiro Moriya, Hamamatsu (JP); Akinori Saito, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 368 days.

(21) Appl. No.: 17/346,468

(22) Filed: Jun. 14, 2021

(65) Prior Publication Data

US 2021/0389400 A1 Dec. 16, 2021

(30) Foreign Application Priority Data

Jun. 16, 2020 (JP) ................................ 2020-103967

(51) Int. Cl.
*A61B 5/245* (2021.01)
*A61B 5/055* (2006.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC .... A61B 5/245; A61B 5/055; G01R 33/0017; G01R 33/26
See application file for complete search history.

(56) References Cited

U.S. PATENT DOCUMENTS 8,305,078 B2 * 11/2012 Savukov ................ G01R 33/26
324/309
8,519,705 B2 * 8/2013 Savukov ................ G01R 33/26
324/304
(Continued)

FOREIGN PATENT DOCUMENTS

JP 5823195 B2 * 11/2015 ......... A61B 5/04008

OTHER PUBLICATIONS

Rainer Körber et al., "SQUIDs in biomagnetism: a roadmap towards improved healthcare", Supercond. Sci. Technol. 113001 (30pp), 2016 vol. 29, p. 1-p. 30.
(Continued)

*Primary Examiner* — Colin T. Sakamoto
(74) *Attorney, Agent, or Firm* — Faegre Drinker Biddle & Reath LLP

(57) ABSTRACT

A brain measurement apparatus includes: a magnetoencephalograph including optically pumped magnetometers, magnetic sensors for measuring a static magnetic field at positions of the optically pumped magnetometers, and a nulling coil for canceling the static magnetic field; an MRI apparatus including a permanent magnet, a gradient magnetic field coil, a transmission coil, and a receive coil for detecting a nuclear magnetic resonance signal; and a control device that, when measuring the brain's magnetic field, controls a current to be supplied to the nulling coil based on measured values of the magnetic sensors and operates so as to cancel a static magnetic field at the position of each of the optically pumped magnetometers and, when measuring an MR image, controls the gradient magnetic field by controlling a current to be supplied to the gradient magnetic field coil and generates an MR image based on an output of the receive coil.

12 Claims, 5 Drawing Sheets

(51) Int. Cl.
  G01R 33/26 (2006.01)
  G01R 33/48 (2006.01)
  G01R 33/032 (2006.01)
  G01R 33/421 (2006.01)
  A61B 5/00 (2006.01)
  G01R 33/00 (2006.01)

(52) U.S. Cl.
  CPC ............ A61B 5/245 (2021.01); A61B 5/6803 (2013.01); G01R 33/0017 (2013.01); G01R 33/032 (2013.01); G01R 33/26 (2013.01); G01R 33/4215 (2013.01); *A61B 2562/0223* (2013.01); *A61B 2562/182* (2013.01); *G01R 33/0076* (2013.01)

(56) References Cited

U.S. PATENT DOCUMENTS

| | | | | |
|---|---|---|---|---|
| 2013/0144153 A1* | 6/2013 | Inglis | ............... | A61B 5/055 600/409 |
| 2016/0223622 A1* | 8/2016 | Yu | ............... | G01R 33/0354 |
| 2018/0031651 A1* | 2/2018 | Iaia | ............... | G01R 33/56563 |
| 2020/0057115 A1* | 2/2020 | Jiménez-Martínez | ............... | G01R 33/26 |
| 2020/0072916 A1* | 3/2020 | Alford | ............... | G01R 33/0017 |
| 2020/0249295 A1* | 8/2020 | Punzo | ............... | G01R 33/56563 |
| 2020/0260976 A1* | 8/2020 | Sasaki | ............... | A61B 5/4076 |
| 2020/0334559 A1* | 10/2020 | Anderson | ............... | G06N 20/00 |
| 2021/0247471 A1* | 8/2021 | Shapiro | ............... | A61B 5/4064 |
| 2021/0247648 A1* | 8/2021 | Zhang | ............... | G02F 1/134345 |
| 2021/0369166 A1* | 12/2021 | Alford | ............... | A61B 5/6803 |
| 2022/0091200 A1* | 3/2022 | Gerginov | ............... | G01R 33/26 |

OTHER PUBLICATIONS

Joonas Iivanainen et al., "On-scalp MEG system utilizing an actively shielded array of optically-pumped magnetometers", NeuroImage Elsevier, 2019 vol. 194, p. 244-p. 258.

Elena Boto et al., "Moving magnetoencephalography towards real-world applications with a wearable system", nature, Mar. 29, 2018 vol. 555.

* cited by examiner

BRAIN MEASUREMENT APPARATUS AND BRAIN MEASUREMENT METHOD

TECHNICAL FIELD

Aspects of the present disclosure relate to a brain measurement apparatus and a brain measurement method.

BACKGROUND

In the related art, as a magnetoencephalograph, a superconducting quantum interference device (SQUID) has been used to measure a small magnetic field of the brain. In recent years, a magnetoencephalograph using an optically pumped magnetometer instead of the SQUID has been studied. The optically pumped magnetometer measures small magnetic field by using the spin polarization of alkali metal atoms excited by optical pumping. For example, Japanese Patent No. 5823195 discloses a magnetoencephalograph using an optical pumping magnetometer. In addition, recently, research has also been conducted to integrate a magnetoencephalograph and a magnetic resonance imaging (MRI) apparatus using the SQUID (see "SQUIDs in biomagnetism: a roadmap towards improved healthcare", Supercond. Sci. Technol. 29 (2016) 113001 (30 pp)).

SUMMARY

Here, the measurement by the magnetoencephalograph needs to be performed in a state in which an environmental magnetic field including the geomagnetic field is reduced, in order to avoid the influence of the magnetic field stronger than the brain's magnetic field. On the other hand, the measurement by the MRI needs to be performed in a state in which a static magnetic field, a gradient magnetic field, and the like are generated. When trying to realize an apparatus in which a magnetoencephalograph and an MRI apparatus are integrated, it is required to efficiently realize the reduction of environmental magnetic field and the application of a static magnetic field, a gradient magnetic field, and the like.

The present invention has been made in view of the above circumstances, and it is an object of the present invention to provide a brain measurement apparatus and a brain measurement method capable of efficiently realizing brain's magnetic field measurement and MRI measurement.

A brain measurement apparatus according to one aspect of the present invention includes: a magnetoencephalograph including multiple optically pumped magnetometers configured to measure a brain's magnetic field, multiple magnetic sensors for static magnetic field cancellation configured to measure a static magnetic field at a position of each of the multiple optically pumped magnetometers, and a static magnetic field nulling coil for canceling the static magnetic field; an MRI apparatus including a permanent magnet for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse; and a controller configured to, when measuring the brain's magnetic field, control a current to be supplied to the static magnetic field nulling coil based on measured values of the multiple magnetic sensors for static magnetic field cancellation and operate so as to cancel a static geomagnetic field and a static magnetic field generated by the permanent magnet at the position of each of the multiple optically pumped magnetometers and, when measuring an MR image, control the gradient magnetic field by controlling a current to be supplied to the gradient magnetic field coil and generates an MR image based on an output of the receive coil.

In addition, a brain measurement method according to another aspect of the present invention is a brain measurement method using a magnetoencephalograph including multiple optically pumped magnetometers configured to measure a brain's magnetic field, multiple magnetic sensors for static magnetic field cancellation configured to measure a static magnetic field at a position of each of the multiple optically pumped magnetometers, and a static magnetic field nulling coil for canceling the static magnetic field and an MRI apparatus including a permanent magnet for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse. The brain measurement method includes: when measuring the brain's magnetic field, controlling a current to be supplied to the static magnetic field nulling coil based on measured values of the multiple magnetic sensors for static magnetic field cancellation and operating so as to cancel a static geomagnetic field and a static magnetic field generated by the permanent magnet at the position of each of the multiple optically pumped magnetometers; and when measuring an MR image, controlling the gradient magnetic field by controlling a current to be supplied to the gradient magnetic field coil and generating an MR image based on an output of the receive coil.

According to the above one aspect or another aspect, the static magnetic field at the position of each of the multiple optically pumped magnetometers for measuring the brain's magnetic field is measured. Then, when measuring the brain's magnetic field, the current flowing through the static magnetic field nulling coil is controlled based on the multiple measured values of the static magnetic field, the magnetic field is generated in each coil, and the static geomagnetic field and the static magnetic field generated by the permanent magnet are canceled by the magnetic field generated in the static magnetic field nulling coil at the positions of the multiple optically pumped magnetometers. As a result, since the static magnetic field at the positions of the multiple optically pumped magnetometers is canceled, the multiple optically pumped magnetometers can measure the brain's magnetic field in a state in which the influence of the environmental magnetic field is avoided. At this time, the static geomagnetic field and the static magnetic field generated by the permanent magnet can be collectively canceled by the static magnetic field nulling coil.

On the other hand, according to the above one aspect or another aspect, when measuring the MR image, the static magnetic field is applied by the permanent magnet and the gradient magnetic field is applied by controlling the current flowing through the gradient magnetic field coil, and the nuclear magnetic resonance signal generated by the transmission of the transmission pulse is detected by the receive coil. As a result, the MR image can be measured based on the output of the receive coil. In particular, since the permanent magnet is used to generate the static magnetic field, the size of the apparatus can be reduced and the power consumption can be reduced compared with a configuration in which the static magnetic field is generated by the electromagnet.

According to such a brain measurement apparatus and a brain measurement method, it is possible to efficiently realize brain's magnetic field measurement and MRI measurement using the same apparatus. In particular, in MRI measurement, a superconducting coil is not required, a magnetic shield room for reducing magnetic noise during the measurement of the brain's magnetic field is also not required, and a coolant such as liquid helium required when using the SQUID is also not required. Therefore, it is possible to reduce the size and cost. In addition, since the brain's magnetic field measurement and the MRI measurement can be sequentially performed on the same subject using the same apparatus, it is possible to reduce registration errors in both measurement results.

DETAILED DESCRIPTION

Figure 1:
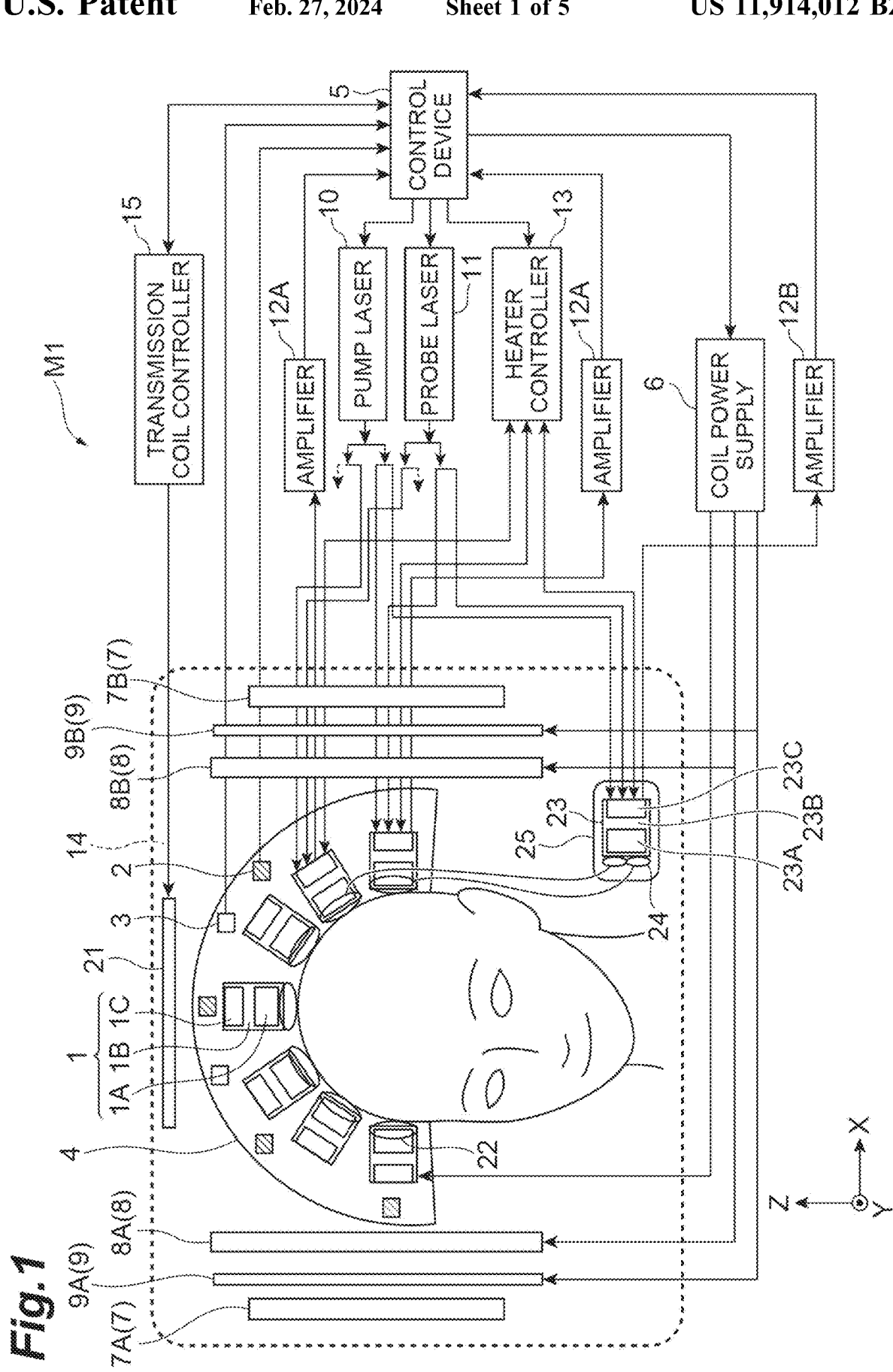
FIG. 1 is a schematic view showing the configuration of a brain measurement apparatus according to an embodiment.

Hereinafter, an embodiment for carrying out the present invention will be described in detail with reference to the accompanying diagrams. In the description of the diagrams, the same elements are denoted by the same reference numerals, and the repeated description thereof will be omitted.

Figure 2:
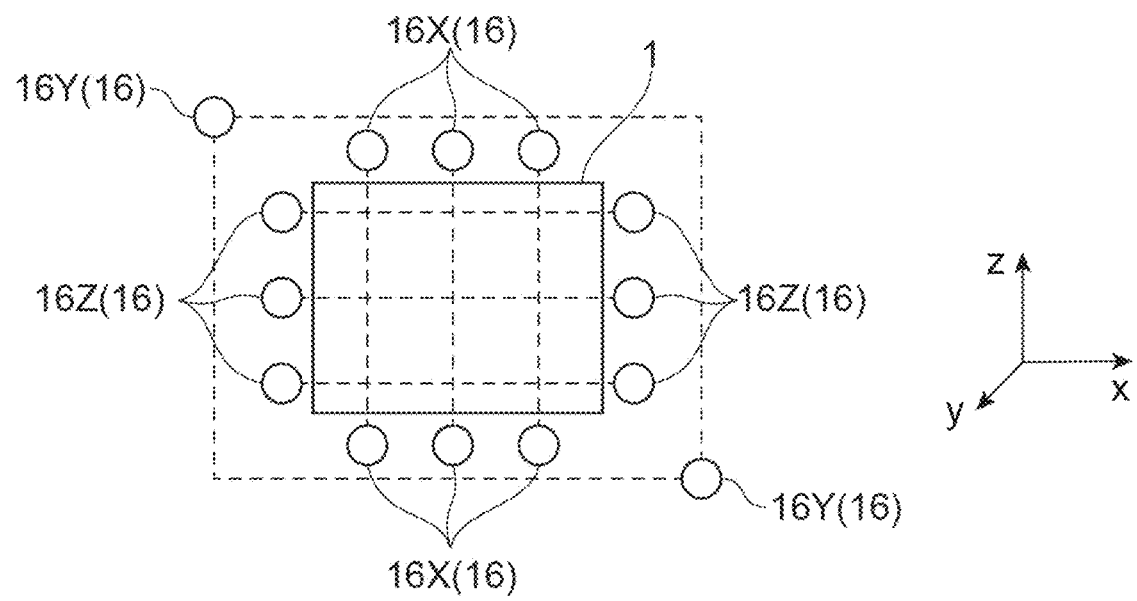
FIG. 2 is a schematic view showing the configuration of a static magnetic field nulling coil according to the embodiment.

FIG. 1 is a schematic view showing the configuration of a brain measurement apparatus M1 according to an embodiment, and FIG. 2 is a schematic diagram showing the configuration of a static magnetic field nulling coil 16 included in the brain measurement apparatus M1. The brain measurement apparatus M1 is an apparatus for measuring a brain's magnetic field and a magnetic resonance (MR) image for a subject. The brain measurement apparatus M1 includes: a magnetoencephalograph module having multiple optically pumped magnetometer (OPM) modules 1, multiple magnetic sensors for static magnetic field cancellation 2, multiple magnetic sensors for active shield 3, a non-magnetic frame 4, a static magnetic field nulling coil 16, and a pair of active shield coils 9; and an MRI module having a pair of permanent magnets 7, a pair of gradient magnetic field coils 8, a transmission coil 21, a receive coil 22, an OPM module 23, and an output coil 24. In addition, the brain measurement apparatus M1 includes a control device 5, a coil power supply 6, a pump laser 10, a probe laser 11, amplifiers 12A and 12B, a heater controller 13, an electromagnetic shield 14, and a transmission coil controller 15.

In the following description, a direction approximately parallel to the central axis of the head of the subject is defined as a Z-axis direction and directions perpendicular to the Z axis and perpendicular to each other are defined as an X-axis direction and a Y-axis direction.

Each OPM module 1 includes a optically pumped magnetometer 1A, a heat insulating material 1B, and a read circuit 1C. The multiple OPM modules 1 are arranged at predetermined intervals along the scalp, for example.

The optically pumped magnetometer 1A is a sensor that measures a brain's magnetic field by using optical pumping, and has a sensitivity of, for example, about 10 fT to 10 pT. The heat insulating material 1B prevents heat transfer of the optically pumped magnetometer 1A. The read circuit 1C is a circuit for acquiring the detection result of the optically pumped magnetometer 1A. The pump laser 10 emits pump light to a cell containing alkali metal vapor to excite the alkali metal. The excited alkali metal is in a spin polarization state, and when this receives magnetic field, the inclination of the spin polarization axis of the alkali metal atom changes according to the magnetic field. The inclination of the spin polarization axis is detected by probe light emitted separately from the pump light. In addition, the optically pumped magnetometer 1A is configured such that a predetermined bias magnetic field is applied in the emission direction of the pump light by the static magnetic field nulling coil 16, which is provided for each OPM module 1, so as to be sensitive to a magnetic field having a frequency included in the range of 0 to 200 Hz. The read circuit 1C receives probe light passing through the alkali metal vapor by a photodiode and acquires the detection result. The read circuit 1C outputs the detection result to the amplifier 12A.

The optically pumped magnetometer 1A may be, for example, an axial gradiometer. The axial gradiometer has a measurement region and a reference region in a direction perpendicular to the scalp (measurement location) of the subject and coaxially. The measurement region is, for example, a location closest to the scalp of the subject among locations where the axial gradiometer measures the brain's magnetic field. The reference region is, for example, a location away from the measurement region by a predetermined distance (for example, 3 cm) in a direction away from the scalp of the subject, among locations where the axial gradiometer measures the brain's magnetic field. The axial gradiometer outputs the respective measurement results in the measurement region and the reference region to the amplifier 12A. Here, when common mode noise is included, its influence is shown in each of the output result of the measurement region and the output result of the reference region. Common mode noise is removed by acquiring the difference between the output result of the measurement region and the output result of the reference region. By removing the common mode noise, the optically pumped magnetometer 1A can obtain a sensitivity of about 10 fT/√Hz, for example, when performing measurement in a magnetic noise environment of 1 pT.

The magnetic sensor for static magnetic field cancellation 2 is a sensor that measures a composite static magnetic field including a static geomagnetic field and a static magnetic field generated by the permanent magnet 7 at a position corresponding to the optically pumped magnetometer 1A, and is, for example, a flux gate sensor having a sensitivity of about 1 nT to 10 mT. The position corresponding to the optically pumped magnetometer 1A is a position around (near) the region where the optically pumped magnetometer 1A is arranged. The magnetic sensor for static magnetic field cancellation 2 may be provided so as to correspond to the optically pumped magnetometer 1A in a one-to-one manner, or may be provided so as to correspond in a one-to-many manner (one magnetic sensor for static magnetic field cancellation 2 for multiple optically pumped magnetometers 1A). The magnetic sensor for static magnetic field cancellation 2 measures not only the static magnetic field but also the gradient magnetic field of the geomagnetism (hereinafter, simply referred to as "gradient magnetic field"), and outputs the measured values to the control device 5. The measured value of the magnetic sensor for static magnetic field cancellation 2 can be expressed by a vector having a direction and a magnitude. The magnetic sensor for static magnetic field cancellation 2 may continuously perform measurement and output at predetermined time intervals.

The magnetic sensor for active shield 3 is a sensor that measures a fluctuating magnetic field at a position corresponding to the optically pumped magnetometer 1A, and is, for example, a optically pumped magnetometer having a sensitivity of about 100 fT to 10 nT and different from the optically pumped magnetometer 1A. The position corresponding to the optically pumped magnetometer 1A is a position around (near) the region where the optically pumped magnetometer 1A is arranged. The magnetic sensor for active shield 3 may be provided so as to correspond to the optically pumped magnetometer 1A in a one-to-one manner, or may be provided so as to correspond in a one-to-many manner (one magnetic sensor for active shield 3 for the multiple optically pumped magnetometers 1A). The magnetic sensor for active shield 3 measures a magnetic field of a noise (AC) component of, for example, 200 Hz or less as a fluctuating magnetic field, and outputs the measured value to the control device 5. The measured value of the magnetic sensor for active shield 3 can be expressed by a vector having a direction and a magnitude. The magnetic sensor for active shield 3 may continuously perform measurement and output at predetermined time intervals.

The non-magnetic frame 4 is a frame that covers the entire scalp of the subject whose brain's magnetic field is to be measured, and is formed of a non-magnetic material such as graphite whose relative magnetic permeability is close to 1 and accordingly does not affect the magnetic field distribution. The non-magnetic frame 4 can be, for example, a helmet-type frame that surrounds the entire scalp of the subject and is attached to the head of the subject. The multiple optically pumped magnetometers 1A are fixed to the non-magnetic frame 4 so as to be close to the scalp of the subject. In addition, the magnetic sensor for static magnetic field cancellation 2 is fixed to the non-magnetic frame 4 so that a static magnetic field at the position of each of the multiple optically pumped magnetometers 1A can be measured, and the magnetic sensor for active shield 3 is fixed to the non-magnetic frame 4 so that a fluctuating magnetic field at the position of each of the multiple optically pumped magnetometers 1A can be measured. Since a change in the magnetic field strength according to the position of the fluctuating magnetic field is smaller than that in the case of the static magnetic field, a smaller number of magnetic sensors for active shield 3 than the number of magnetic sensors for static magnetic field cancellation 2 may be fixed to the non-magnetic frame 4.

In addition, the receive coil 22 for detecting a nuclear magnetic resonance signal for MR image measurement is fixed to the scalp side of the subject of the multiple optically pumped magnetometers 1A inside the non-magnetic frame 4. The receive coil 22 detects the nuclear magnetic resonance signal of the proton, which will be described later, and converts the nuclear magnetic resonance signal into an electric current. In order to improve the detection sensitivity of the nuclear magnetic resonance signal, it is preferable that the receive coil 22 is provided on the side of the optically pumped magnetometer 1A close to the scalp of the head of the subject.

In addition, the static magnetic field nulling coil 16 for canceling the static magnetic field and applying a predetermined bias magnetic field to the optically pumped magnetometers 1A when measuring the brain's magnetic field is provided around each of the multiple the OPM modules 1 including the optically pumped magnetometer 1A in the non-magnetic frame 4. The static magnetic field nulling coil 16 includes coil systems, which are arranged so as to be perpendicular to each other and which can apply magnetic fields in three directions perpendicular to each other (for example, a three-axis Helmholtz coil or a planar coil system). Specifically, as shown in FIG. 2, the static magnetic field nulling coil 16 includes coil systems 16X, 16Y, and 16Z. The coil systems 16X, 16Y, and 16Z are arranged as shown by dotted lines with respect to the OPM module 1. In this manner, the coil systems 16X, 16Y, and 16Z are arranged so as to be perpendicular to each other and surround each OPM module 1 (optically pumped magnetometer 1A). The coil system 16X is a coil for canceling the component of the static magnetic field in the x-axis direction. Similarly, the coil systems 16Y and 16Z are coils for canceling the components of the static magnetic field in the y-axis direction and the z-axis direction, respectively.

The static magnetic field nulling coil 16 cancels the static magnetic field at the position of the optically pumped magnetometer 1A, and at the same time, applies a predetermined bias magnetic field to the optically pumped magnetometer 1A. The static magnetic field nulling coil 16 generates a magnetic field according to the current supplied from the coil power supply 6 to cancel the static magnetic field. The coil systems 16X, 16Y, and 16Z included in the static magnetic field nulling coil 16 generate magnetic fields, which are opposite to the static magnetic field at the position of the optically pumped magnetometer 1A and have approximately the same magnitude as the static magnetic field, according to the current supplied from the coil power supply 6. The direction of the magnetic field is, for example, the X-axis direction, the Y-axis direction, and the Z-axis direction. In addition, the static magnetic field nulling coil 16 generates a predetermined bias magnetic field along the emission direction of the pump light for the optically pumped magnetometer 1A according to the current supplied from the coil power supply 6. The static magnetic field at the position of the optically pumped magnetometer 1A is canceled by a magnetic field generated by the static magnetic field nulling coil 16, the magnetic field being opposite to the static magnetic field and having approximately the same magnitude as the static magnetic field.

The transmission coil 21 is a coil for emitting an RF pulse (transmission pulse) having a predetermined frequency (for example, about 300 kHz) to the head of the subject during MR image measurement. The transmission coil 21 is arranged above the head of the subject outside the non-magnetic frame 4, for example.

The output coil 24 is electrically connected to both ends of the receive coil 22 through a cable, and receives a current flowing through both ends of the receive coil 22, converts the current into a magnetic signal again, and outputs the magnetic signal.

Similar to the OPM module 1, the OPM module 23 includes a optically pumped magnetometer 23A, a heat insulating material 23B, and a read circuit 23C. The OPM module 23 is housed in, for example, a magnetic shield 25 that shields a static magnetic field, which will be described later, outside the non-magnetic frame 4 together with the output coil 24. The magnetic shield 25 is formed of, for example, mu-metal having a relative magnetic permeability of more than 1.

The optically pumped magnetometer 23A is a sensor that measures a magnetic signal using optical pumping. In addition, the optically pumped magnetometer 23A is configured such that a predetermined bias magnetic field is applied in the emission direction of pump light so as to be sensitive to a magnetic field having a frequency included in the range of 20 kHz to 500 kHz. For example, a bias magnetic field of about 40 µT is applied so as to be sensitive to the frequency of 300 kHz of the electromagnetic wave emitted by the proton. The read circuit 23C outputs the detection result of the optically pumped magnetometer 23A to the amplifier 12B.

Figure 3:
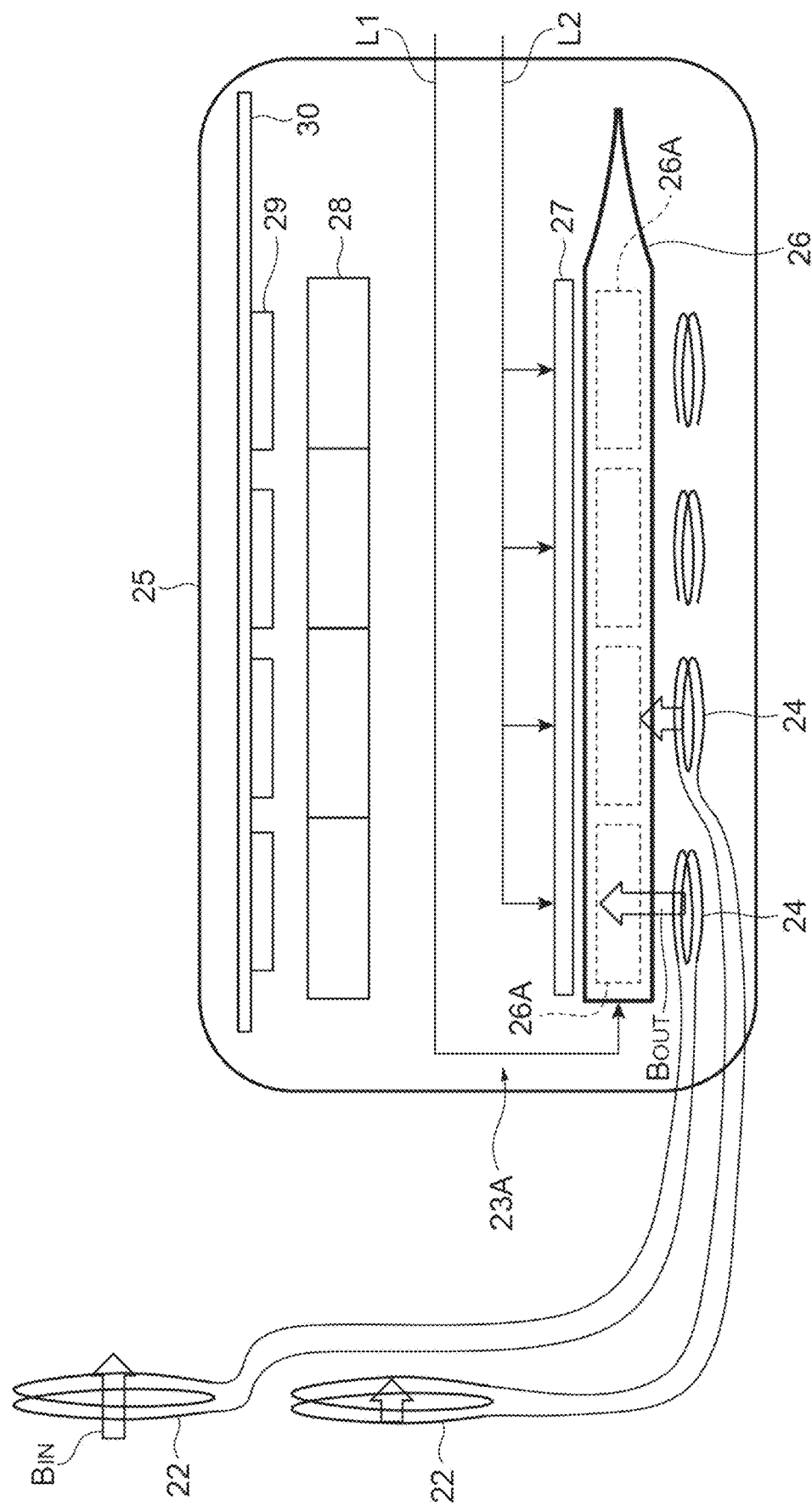
FIG. 3 is a schematic view showing the configuration of an OPM module according to the embodiment.

FIG. 3 shows a specific example of the configuration of the OPM module 23. The optically pumped magnetometer 23A includes a longitudinal cell 26 filled with a gas containing an alkali metal whose direction of polarization changes with a magnetic field to be measured, a heater 27 that heats the entire cell 26 to a predetermined temperature (for example, 180°), a polarization beam splitter 28, and a photodetector 29. Pump light L1 is introduced into the cell 26 from the outside along the longitudinal direction of the inside of the cell 26. In addition, along a direction perpendicular to the longitudinal direction, probe light L2 from the outside is branched and emitted to multiple crossing regions 26A (for example, four crossing regions 26A) divided in the longitudinal direction. The polarization angle of the probe light L2 transmitted through the crossing regions 26A is detected by the polarization beam splitter 28 and the photodetector 29 provided corresponding to each of the crossing regions 26A. That is, the polarization beam splitter 28 separates the probe light L2 into two linearly polarized components perpendicular to each other, and the photodetector 29 detects the intensities of the two linearly polarized components using two built-in photodiodes (PDs) and detects the polarization angle of the probe light L2 based on the ratio of the detected intensities. A circuit board 30 is further provided in the OPM module 23. Through the read circuit 23C in the circuit board 30, the polarization angle of the probe light L2 detected for each crossing region 26A is output.

In the magnetic shield 25, the output coil 24 is fixed so as to face each crossing region 26A of the cell 26 in the OPM module 23 having the above-described configuration. With such a configuration, a magnetic signal $B_{OUT}$ generated by the output coil 24 based on the electromagnetic field $B_{OUT}$ detected by the receive coil 22 is detected based on the polarization angle of the probe light L2 that changes according to the inclination of the spin polarization axis of the alkali metal atom. Here, in the example of FIG. 3, the number of divided crossing regions 26A is four, but may be changed to any number. In addition, multiple cells 26 may be provided in parallel, so that the crossing regions 26A are arrayed in a two-dimensional manner (for example, 4×4=16).

When measuring the brain's magnetic field, the control device 5 determines currents for various coils based on the measured values output from the magnetic sensor for static magnetic field cancellation 2 and the magnetic sensor for active shield 3, and outputs a control signal for outputting each of the currents to the coil power supply 6. Based on the measured values of the multiple magnetic sensors for static magnetic field cancellation 2, the control device 5 determines a current for the static magnetic field nulling coil 16 so as to generate a magnetic field for canceling a static magnetic field. In addition, based on the measured values of the multiple magnetic sensors for active shield 3, the control device 5 determines a current for the active shield coil 9 so as to generate a magnetic field for canceling a fluctuating magnetic field. The control device 5 outputs a control signal corresponding to the determined current to the coil power supply 6.

Specifically, based on the measured values of the multiple magnetic sensors for static magnetic field cancellation 2, the control device 5 determines a current for the static magnetic field nulling coil 16 so as to generate a magnetic field opposite to the static magnetic field at the position of the optically pumped magnetometer 1A and having approximately the same magnitude as the static magnetic field. This can be realized by measuring the measured value of the magnetic sensor for static magnetic field cancellation 2 and the magnetic field strength at the optically pumped magnetometer 1A in advance. The control device 5 outputs a control signal (control signal for static magnetic field cancellation) corresponding to the determined current of the static magnetic field nulling coil 16 to the coil power supply 6.

In addition, the control device 5 determines a current for the active shield coil 9 so that the average value of the measured values of the multiple magnetic sensors for active shield 3 approaches zero (as a result, a magnetic field opposite to the fluctuating magnetic field at the position of the optically pumped magnetometer 1A and having approximately the same magnitude as the fluctuating magnetic field is generated). The control device 5 outputs a control signal (control signal for fluctuating magnetic field cancellation) corresponding to the determined current of the active shield coil 9 to the coil power supply 6.

In addition, the control device 5 obtains information regarding the magnetic field detected by the optically pumped magnetometer 1A by using the signal output from the amplifier 12A. When the optically pumped magnetometer 1A is an axial gradiometer, the control device 5 may remove the common mode noise by acquiring the difference between the output result of the measurement region and the output result of the reference region. In addition, the control device 5 may control operations such as the emission timing and the emission time of the pump laser 10 and the probe laser 11.

In addition, when measuring the MR image, the control device 5 determines a current to be supplied to the gradient magnetic field coil 8 for applying the gradient magnetic field, and outputs a control signal for outputting the current to the coil power supply 6. That is, the control device 5 selectively determines an X-axis direction magnetic field gradient ($dB_x/dX$), a Y-axis direction magnetic field gradient ($dB_x/dY$), and a Z-axis direction magnetic field gradient ($dB_x/dZ$) as a gradient magnetic field to determine a current flowing through the gradient magnetic field coil 8. Therefore, a slicing position in the MR image can be determined, and the position within the slice surface can be encoded by phase encoding and frequency encoding. In addition, when measuring the MR image, the control device 5 outputs a control signal so that no current is supplied to the active shield coil 9 for removing low-frequency noise.

In addition, when measuring the MR image, the control device 5 outputs a control signal, which is for controlling electric power supplied to the transmission coil 21, to the transmission coil controller 15, so that control to emit an RF pulse having a predetermined frequency (for example, about 300 kHz when the strength of the static magnetic field is 7 mT) to the head of the subject is performed. As a result, protons on the slice surface (surface selected by the static magnetic field and the gradient magnetic field) resonate to tilt the spin. Thereafter, the control device 5 controls the electric power of the transmission coil 21 to be turned off.

As a result, it is possible to acquire the MR image by measuring how the spin returns based on the output of the OPM module 23. More specifically, the control device 5 measures the nuclear magnetic resonance signal from the proton by encoding the position with frequency and phase using a known spin echo sequence or gradient echo sequence, and converts the measurement result into an MR image using FFT.

The control device 5 is physically configured to include a memory such as a RAM and a ROM, a processor (arithmetic circuit) such as a CPU, a communication interface, and a storage unit such as a hard disk. Examples of the control device 5 include a personal computer, a cloud server, a smartphone, and a tablet terminal. The control device 5 functions by executing a program stored in the memory on the CPU of the computer system.

The coil power supply 6 outputs a predetermined current to each of the static magnetic field nulling coil 16, the gradient magnetic field coil 8, and the active shield coil 9 in response to the control signal output from the control device 5. Specifically, the coil power supply 6 outputs a current to the static magnetic field nulling coil 16 in response to the control signal relevant to the static magnetic field nulling coil 16. The coil power supply 6 outputs a current to the gradient magnetic field coil 8 in response to the control signal relevant to the gradient magnetic field coil 8. The coil power supply 6 outputs a current to the active shield coil 9 in response to the control signal relevant to the active shield coil 9.

The transmission coil controller 15 is electrically connected to the transmission coil 21, and supplies electric power to the transmission coil 21 in response to the control signal output from the control device 5 so that an electromagnetic wave having a predetermined frequency is emitted.

The permanent magnet 7 is configured to apply a magnetic field having a predetermined strength (for example, 7 mT) in a predetermined direction to the head of the subject as a static magnetic field. The permanent magnet 7 has, for example, a pair of permanent magnets 7A and 7B. The pair of permanent magnets 7A and 7B are arranged with the optically pumped magnetometers 1A interposed therebetween (for example, on the left and right of the subject). The pair of permanent magnets 7A and 7B generate, for example, a static magnetic field in the X-axis direction on the subject's head.

The gradient magnetic field coil 8 is a coil for applying a gradient magnetic field to the head of the subject during MR image measurement. The gradient magnetic field coil 8 generates a gradient magnetic field according to the current supplied from the coil power supply 6. The gradient magnetic field coil 8 has, for example, a pair of gradient magnetic field coils 8A and 8B. The pair of gradient magnetic field coils 8A and 8B are arranged with the optically pumped magnetometers 1A interposed therebetween (for example, on the left and right of the subject). The gradient magnetic field coil 8 generates a gradient magnetic field having a selective gradient in the X-axis direction, the Y-axis direction, and the Z-axis direction according to the current supplied from the coil power supply 6.

The active shield coil 9 is a coil for canceling the fluctuating magnetic field at the position of the optically pumped magnetometer 1A. The active shield coil 9 generates a magnetic field according to the current supplied from the coil power supply 6 to cancel the fluctuating magnetic field. The active shield coil 9 has, for example, a pair of active shield coils 9A and 9B. The pair of active shield coils 9A and 9B are arranged with the optically pumped magnetometers 1A interposed therebetween (for example, on the left and right of the subject). The pair of active shield coils 9A and 9B generate a magnetic field, which is opposite to the fluctuating magnetic field at the position of the optically pumped magnetometer 1A and has approximately the same magnitude as the fluctuating magnetic field, according to the current supplied from the coil power supply 6. The direction of the magnetic field is, for example, the X-axis direction, the Y-axis direction, and the Z-axis direction. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field. In this manner, the active shield coil 9 cancels the fluctuating magnetic field at the position of the optically pumped magnetometer 1A.

The pump laser 10 is a laser device that generates pump light. The pump light emitted from the pump laser 10 is incident on each of the multiple optically pumped magnetometers 1A and the optically pumped magnetometers 23A by fiber branching.

The probe laser 11 is a laser device that generates probe light. The probe light emitted from the probe laser 11 is incident on each of the multiple optically pumped magnetometers 1A and the optically pumped magnetometers 23A by fiber branching.

The amplifier 12A is a device or circuit that amplifies an output result signal from the OPM module 1 (specifically, the read circuit 1C) and outputs the signal to the control device 5.

The amplifier 12B is a device or circuit that amplifies an output result signal from the OPM module 23 (specifically, the read circuit 23C) and outputs the signal to the control device 5.

The heater controller 13 is a temperature adjusting device connected to a heater for heating the cell of the optically pumped magnetometer 1A and the cell of the optically pumped magnetometer 23A and a thermocouple (not shown) for measuring the temperature of each cell. The heater controller 13 adjusts the temperature of each cell by receiving the temperature information of the cell from the thermocouple and adjusting the heating of the heater based on the temperature information.

The electromagnetic shield 14 is a shield member for shielding high-frequency (for example, 10 kHz or higher) electromagnetic noise. For example, the electromagnetic shield 14 is formed of a mesh woven with metal threads, a non-magnetic metal plate such as aluminum, or the like. The electromagnetic shield 14 is arranged so as to surround the OPM modules 1 and 23, the transmission coil 21, the receive coil 22, the output coil 24, the magnetic sensor for static magnetic field cancellation 2, the magnetic sensor for active shield 3, the non-magnetic frame 4, the permanent magnet 7, the gradient magnetic field coil 8, the active shield coil 9, and the static magnetic field nulling coil 16. The electromagnetic shield 14 can prevent noise in the 300 kHz band, which is a measurement frequency, from entering the receive coil 22 to increase the noise during MR image measurement. In addition, it is possible to prevent high-frequency noise from entering the optically pumped magnetometer 1A to cause an unstable operation during the measurement of the brain's magnetic field.

Figure 4:
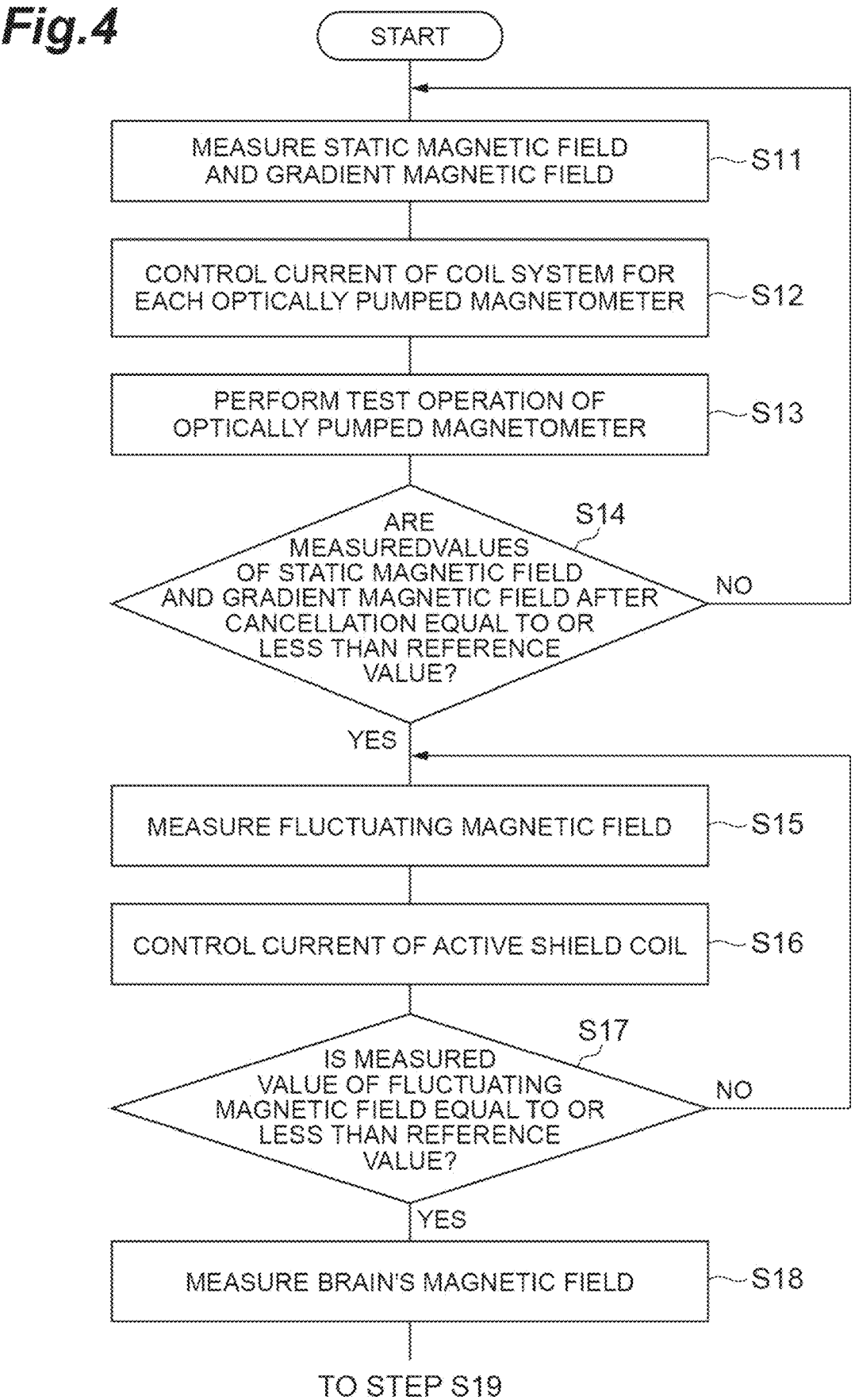
FIG. 4 is a flowchart showing the operation of the brain measurement apparatus according to the embodiment.
Figure 5:
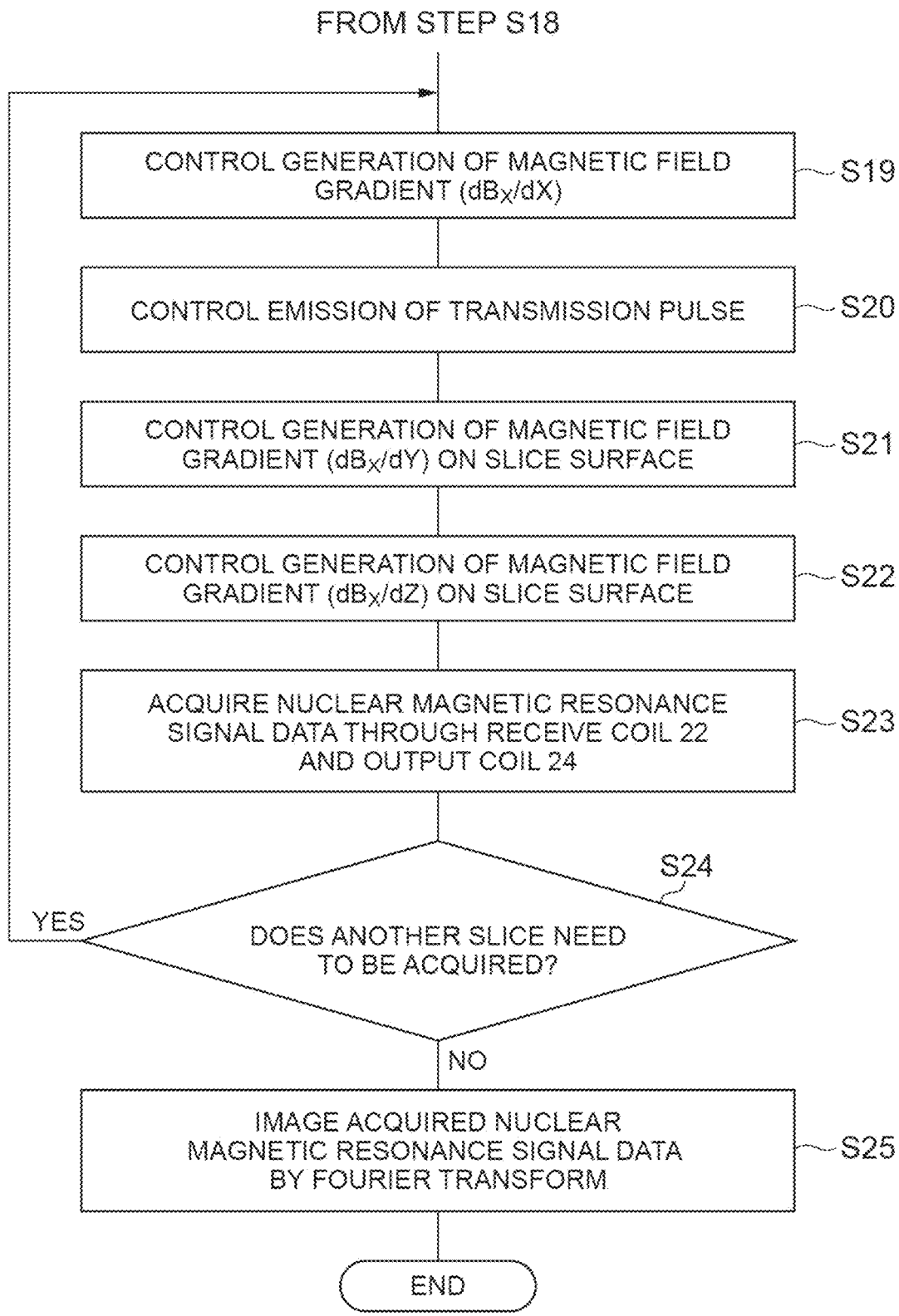
FIG. 5 is a flowchart showing the operation of the brain measurement apparatus according to the embodiment.

Next, a brain measurement method using the brain measurement apparatus M1 according to the embodiment will be described with reference to FIGS. 4 and 5. FIGS. 4 and 5 are flowcharts showing the operation of the brain measurement apparatus M1.

First, referring to FIG. 4, when the measurement of the brain's magnetic field starts with the non-magnetic frame 4 attached to the subject, the magnetic sensor for static magnetic field cancellation 2 measures a static magnetic field and its gradient magnetic field (step S11). The magnetic sensor for static magnetic field cancellation 2 measures the static magnetic field and the gradient magnetic field at each position of the optically pumped magnetometer 1A, and outputs the measured values to the control device 5.

The control device 5 and the coil power supply 6 control a current for the static magnetic field nulling coil 16 for each optically pumped magnetometer 1A (step S12). The control device 5 determines a current for the static magnetic field nulling coil 16 based on the measured value of the magnetic sensor for static magnetic field cancellation 2 so that a magnetic field opposite to each component of the static magnetic field in the three directions (x axis, y axis, and z axis) at the position of the optically pumped magnetometer 1A and having approximately the same magnitude as each component of the static magnetic field in the three directions is generated. This can be realized by measuring the measured value of the magnetic sensor for static magnetic field cancellation 2 and the magnetic field strength at the optically pumped magnetometer 1A in advance. The control device 5 outputs a control signal corresponding to the determined currents of the coil systems 16X, 16Y, and 16Z to the coil power supply 6. The coil power supply 6 outputs a predetermined current to each of the coil systems 16X, 16Y, and 16Z in response to the control signal output from the control device 5. Each of the coil systems 16X, 16Y, and 16Z generates a magnetic field according to the current supplied from the coil power supply 6. The components of the static magnetic field in the three directions at the position of the optically pumped magnetometer 1A are canceled by the magnetic fields generated by the coil systems 16X, 16Y, and 16Z, the magnetic fields being opposite to the components of the static magnetic field in the three directions and having approximately the same magnitude as the components of the static magnetic field in the three directions.

Then, a test operation of the optically pumped magnetometer 1A is performed (step S13). The optically pumped magnetometer 1A acquires the measured value of the remaining magnetic field by the test operation and outputs the measured value to the control device 5. The measured value of the magnetic field is a value measured by the optically pumped magnetometer 1A after the static magnetic field and the gradient magnetic field are canceled by the static magnetic field nulling coil 16.

The control device 5 determines whether or not the measured values of the static magnetic field and the gradient magnetic field after the cancellation are equal to or less than the reference value (step S14). The measured values of the static magnetic field and the gradient magnetic field after the cancellation are values measured by the optically pumped magnetometer 1A after the static magnetic field and the gradient magnetic field are canceled by the static magnetic field nulling coil 16. The reference value is the magnitude of the magnetic field in which the optically pumped magnetometer 1A normally operates, and can be set to, for example, 1 nT. If the measured values of the static magnetic field and the gradient magnetic field are not equal to or less than the reference value ("NO" in step S14), the process returns to step S11. If the measured value of the static magnetic field is equal to or less than the reference value ("YES" in step S14), the process proceeds to step S15.

The magnetic sensor for active shield 3 measures a fluctuating magnetic field (step S15). The magnetic sensor for active shield 3 measures a fluctuating magnetic field at each position of the optically pumped magnetometer 1A and outputs the measured value to the control device 5.

The control device 5 and the coil power supply 6 control a current for the active shield coil 9 (step S16). The control device 5 determines a current for the active shield coil 9 based on the measured value of the magnetic sensor for active shield 3 so that a magnetic field opposite to the fluctuating magnetic field at the position of the optically pumped magnetometer 1A and having approximately the same magnitude as the fluctuating magnetic field is generated. More specifically, the control device 5 determines a current for the active shield coil 9 so that the average value of the measured values of the multiple magnetic sensors for active shield 3 approaches zero, for example. The control device 5 outputs a control signal corresponding to the determined current to the coil power supply 6. The coil power supply 6 outputs a predetermined current to the active shield coil 9 in response to the control signal output from the control device 5. The active shield coil 9 generates a magnetic field according to the current supplied from the coil power supply 6. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field.

The control device 5 determines whether or not the measured value of the fluctuating magnetic field after the cancellation is equal to or less than the reference value (step S17). The measured value of the fluctuating magnetic field after the cancellation is a value measured by the magnetic sensor for active shield 3 after the fluctuating magnetic field is canceled by the active shield coil 9. The reference value is a noise level at which the brain's magnetic field can be measured, and can be set to, for example, 1 pT. If the measured value of the fluctuating magnetic field is not less than or equal to the reference value ("NO" in step S17), the process returns to step S15. If the measured value of the fluctuating magnetic field is equal to or less than the reference value ("YES" in step S17), the process proceeds to step S18.

The optically pumped magnetometer 1A measures a brain's magnetic field (step S18). The control device 5 outputs the acquired measurement result to a predetermined output destination. The predetermined output destination may be a memory of the control device 5, a storage device of the control device 5 such as a hard disk, an output device of the control device 5 such as a display, or an external device such as a terminal device connected through a communication interface. Since the static magnetic field and the fluctuating magnetic field at the position of the optically pumped magnetometer 1A are canceled so as to be equal to or less than a predetermined reference value, the optically pumped magnetometer 1A can measure the brain's magnetic field in a state in which the influence of the static magnetic field and the influence of the fluctuating magnetic field are avoided.

Moving to FIG. 5, when MR image measurement starts subsequently with the non-magnetic frame 4 attached to the subject, the control device 5 controls the generation of, for example, a magnetic field gradient in the X-axis direction ($dB_X/dX$) by setting the current for the static magnetic field nulling coil 16 to 0, determining a current to be supplied to the gradient magnetic field coil 8 for generating the gradient magnetic field in a state in which a static magnetic field in the X-axis direction is applied to the head of the subject by the permanent magnet 7, and outputting a control signal to the coil power supply 6 (step S19). At the same time, the control device 5 outputs a control signal, which is for controlling the electric power to be supplied to the transmission coil 21, to the transmission coil controller 15 to control the transmission pulse to be emitted to the head of the subject (step S20). As a result, protons on a predetermined slice surface are excited.

In addition, the control device 5 controls the generation of a gradient magnetic field on the slice surface, for example, a Y-axis direction magnetic field gradient ($dB_x/dY$) by determining a current to be supplied to the gradient magnetic field coil 8 for generating the gradient magnetic field and outputting a control signal to the coil power supply 6 (step S21). As a result, phase encoding is performed. Then, the control device 5 controls the generation of a gradient magnetic field on the slice surface, for example, a Z-axis direction magnetic field gradient ($dB_x/dZ$) by determining a current to be supplied to the gradient magnetic field coil 8 for generating the gradient magnetic field and outputting a control signal to the coil power supply 6 (step S22). As a result, frequency encoding is performed.

At the same time, a nuclear magnetic resonance signal from the proton is output from the OPM module 23 through the receive coil 22 and the output coil 24, and the control device 5 acquires the data of the nuclear magnetic resonance signal (step S23). Thereafter, the control device 5 determines whether or not to acquire nuclear magnetic resonance signal data regarding another slice surface (step S24). As a result of the determination, when nuclear magnetic resonance signal data regarding another slice surface is acquired ("YES" in step S24), the process returns to step S19. On the other hand, when nuclear magnetic resonance signal data regarding another slice surface is not acquired ("NO" in step S24), an MR image is acquired by Fourier-transforming the nuclear magnetic resonance signal data acquired so far (step S25). The control device 5 outputs the acquired MR image to a predetermined output destination. The predetermined output destination may be a memory of the control device 5, a storage device of the control device 5 such as a hard disk, an output device of the control device 5 such as a display, or an external device such as a terminal device connected through a communication interface.

Operational Effects

Next, the operational effects of the brain measurement apparatus according to the above embodiment will be described.

According to the brain measurement apparatus M1 according to the present embodiment, the static magnetic field at the position of each of the multiple optically pumped magnetometers 1A for measuring the brain's magnetic field is measured. Then, when measuring the brain's magnetic field, the current flowing through the static magnetic field nulling coil 16 is controlled based on the multiple measured values of the static magnetic field, the magnetic field is generated in the static magnetic field nulling coil 16, and the static geomagnetic field and the static magnetic field generated by the permanent magnet 7 are canceled by the magnetic field generated in the static magnetic field nulling coil 16 at the positions of the multiple optically pumped magnetometers 1A. As a result, since the static magnetic field at the positions of the multiple optically pumped magnetometers 1A is canceled, the multiple optically pumped magnetometers 1A can measure the brain's magnetic field in a state in which the influence of the environmental magnetic field is avoided. At this time, the static geomagnetic field and the static magnetic field generated by the permanent magnet 7 can be collectively canceled by the static magnetic field nulling coil 16.

On the other hand, according to the embodiment described above, when measuring the MR image, the static magnetic field is applied by the permanent magnet 7 and the gradient magnetic field is applied by controlling the current flowing through the gradient magnetic field coil 8, and the nuclear magnetic resonance signal generated by the transmission of the transmission pulse is detected by the receive coil 22. As a result, the MR image can be measured based on the output of the receive coil 22. In particular, since the permanent magnet 7 is used to generate the static magnetic field, the size of the apparatus can be reduced and the power consumption can be reduced compared with a configuration in which the static magnetic field is generated by the electromagnet.

According to such a brain measurement apparatus M1 and a brain measurement method, it is possible to efficiently realize brain's magnetic field measurement and MRI measurement using the same apparatus. In particular, in MRI measurement, since a optically pumped magnetometer is used, a frequency band having a higher sensitivity than the SQUID can be widely adjusted, so that the strength of the applied static magnetic field, that is, the resonance frequency of protons is less limited. A prepolarized coil that has been required since the SQUID operates only at the low resonance frequency, that is, in the low static magnetic field, is not required, and a coolant such as liquid helium required when using the SQUID is also not required. In addition, since the frequency of the signal measured by MRI is also relatively high, a magnetic shield room for reducing magnetic noise during MRI measurement and brain's magnetic field measurement is also not required. As a result, it is possible to reduce the size and cost of the apparatus. In addition, since the time required for prepolarization is approximately the same as the measurement time, the measurement time can also be shortened to ½ in the present embodiment.

In addition, in the present embodiment, since the static magnetic field on the OPM module can be easily turned on and off by controlling the current flowing through the static magnetic field nulling coil 16, it is possible to perform switching between the brain's magnetic field measurement and the MRI measurement in a short time. Therefore, since the brain's magnetic field measurement and the MRI measurement can be sequentially performed on the same subject using the same apparatus, it is possible to reduce registration errors in both measurement results.

In addition, in the present embodiment, when measuring the brain's magnetic field, the fluctuating magnetic fields on the multiple optically pumped magnetometers 1A are canceled by controlling the current supplied to the active shield coil 9 based on the measured value of the fluctuating magnetic field. According to such a configuration, it is possible to measure the brain's magnetic field in a state in which the influence of the fluctuating magnetic field is reliably avoided. As a result, the brain's magnetic field can be measured with high accuracy without using the magnetic shield room.

As described above, according to the present embodiment, since the MRI measurement can be performed in a low magnetic field, a special room is not required, and a tomographic image having a high T1 contrast can be easily acquired. In addition, since the active shield coil 9 is used, it is not necessary to measure the brain's magnetic field in the magnetic shield room. Therefore, since the brain's magnetic field measurement and the MRI measurement can be realized by the same apparatus, both measurements can be sequentially performed while the subject is sitting on a chair or the like. In addition, since the cost of the apparatus can be reduced, the above described measurements can also be performed with the subject on a vehicle or the like. As a result, it is possible to contribute to the diagnosis of mental illness, such as depression and schizophrenia, and neurodegenerative diseases, such as dementia.

Here, the brain measurement apparatus M1 uses the three coil systems 16X, 16Y, and 16Z provided for each of the multiple optically pumped magnetometers 1A for cancellation of the static magnetic field. Therefore, since the current can be finely controlled locally for each of the multiple optically pumped magnetometers 1A, the cancellation accuracy of the static magnetic field is improved. In addition, since only the static magnetic field of a region relevant to the operation of the multiple optically pumped magnetometers 1A is canceled, it is possible to suppress an increase in power consumption due to unnecessary cancellation. In addition, the static magnetic field nulling coil 16 can also cancel the gradient of the environmental magnetic field for each of the multiple optically pumped magnetometers 1A.

In addition, the active shield coil 9 is formed by a pair of coils arranged with multiple optically pumped magnetometers 1A interposed therebetween. According to such a configuration, the fluctuating magnetic field at the positions of the multiple optically pumped magnetometers 1A interposed between the pair of coils is effectively canceled. In this manner, the fluctuating magnetic field can be appropriately canceled by a simple configuration.

In addition, the brain measurement apparatus M1 further includes the output coil 24 electrically connected to the receive coil 22 through a cable and another optically pumped magnetometer 23A for detecting the magnetic signal output by the output coil 24. According to such a configuration, it is possible to avoid the influence of the static magnetic field applied at the time of MRI measurement on the detection signal in another optically pumped magnetometer 23A, so that the accuracy of MR image measurement can be improved. That is, for example, the frequency of the nuclear magnetic resonance signal generated by protons when a static magnetic field of 7 mT is applied is about 300 kHz, and it is necessary to apply a bias magnetic field of about 40 µT in order to give sensitivity to this frequency in the optically pumped magnetometer 23A. When the optically pumped magnetometer 23A is arranged near the head of the subject, it is difficult to achieve both such a bias magnetic field and a static magnetic field.

In the present embodiment, since the receive coil 22 having no sensitivity to the static magnetic field can be arranged near the head and the optically pumped magnetometer 23A can be arranged away from the head, it is possible to detect the nuclear magnetic resonance signal with high sensitivity.

In addition, the multiple optically pumped magnetometers 1A are axial gradiometers having a measurement region and a reference region in a direction perpendicular to the scalp of the subject and coaxially. According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

In addition, the multiple optically pumped magnetometers 1A, the multiple magnetic sensors for static magnetic field cancellation 2, the multiple magnetic sensors for active shield 3, and the receive coil 22 are fixed to the helmet-type non-magnetic frame 4 attached to the head of the subject. According to such a configuration, the non-magnetic frame 4 attached to the head and the sensors 2 and 3 and the receive coil 22 fixed to the non-magnetic frame 4 move according to the movement of the head of the subject. Therefore, even when the head of the subject moves, it is possible to appropriately cancel the static magnetic field at the positions of the multiple optically pumped magnetometers 1A, measure the brain's magnetic field, and perform MRI measurement. As a result, it is possible to suppress registration errors in both measurements.

In addition, the electromagnetic shield 14 for shielding high-frequency electromagnetic noise may be further provided. According to such a configuration, it is possible to prevent high-frequency electromagnetic noise, which is not a measurement target of the magnetoencephalograph, from entering the multiple optically pumped magnetometers 1A. As a result, the measurement of the brain's magnetic field by the multiple optically pumped magnetometers 1A can be stably performed. At the same time, it is possible to prevent noise in the 300 kHz band, which is the measurement frequency of MRI, from entering the receive coil 22 to increase the noise in the MRI measurement.

In addition, the multiple optically pumped magnetometers 1A are configured to be applied a bias magnetic field so as to be sensitive to frequencies included in the range of 0 to 200 Hz, and another optically pumped magnetometer 23A is configured to be applied a bias magnetic field so as to be sensitive to frequencies included in the range of 20 kHz to 500 kHz. With such a configuration, the measurement sensitivity of the brain's magnetic field can be increased, and at the same time, the accuracy of the MRI measurement can also be improved.

Modification Examples

The above description has been made in detail based on the embodiment of the present disclosure. However, the present disclosure is not limited to the embodiment described above. The present disclosure can be modified in various ways without departing from its gist.

Although the active shield coil 9 has been described as having a pair of active shield coils 9A and 9B, the active shield coil 9 may be arranged as a coil system including three pairs of coils for each OPM module 1 (optically pumped magnetometer 1A). In this case, the control device 5 determines a current for the active shield coil 9 so that a magnetic field opposite to the components of the fluctuating magnetic field in the three directions (x axis, y axis, and z axis) at the position of the optically pumped magnetometer 1A and having approximately the same magnitude as the components of the fluctuating magnetic field is generated. The control device 5 outputs a control signal corresponding to the determined current relevant to each of the active shield coils 9, which are arranged as a coil system, to the coil power supply 6. According to such a configuration, the power consumption for canceling the fluctuating magnetic field can be made relatively small.

In addition, when measuring the MR image, the control device 5 may set the current flowing through the static magnetic field nulling coil 16 so as to cancel the gradient geomagnetic field, or may set the current flowing through the static magnetic field nulling coil 16 so as not to cancel the gradient geomagnetic field. Since the magnitude of the gradient magnetic field is about several µT/m in the measurement region and is about two orders of magnitude lower than that of the static magnetic field, high accuracy can be maintained without cancellation when acquiring the MR image.

In addition, the brain measurement apparatus M1 of the embodiment described above may not include the optically pumped magnetometer 23A, or may have a configuration in which the control device 5 directly detects the output from the receive coil 22 through the amplifier.

In addition, the optically pumped magnetometer 1A is not limited to the pump & probe type that uses pump light and probe light, and may be a zero field type optically pumped magnetometer that uses circularly polarized light that also serves as pump light and probe light. In this zero field type, light can be emitted to the cell and a periodic bias magnetic field can be applied to the cell for the lock-in detection of the magnetic field, and the deviation from the zero magnetic field can be measured as the brain's magnetic field.

In addition, in the brain measurement apparatus M1 of the embodiment described above, the position of the non-magnetic frame 4 may be optically measurable. For example, a marker attached to the periphery of the lower end of the non-magnetic frame 4 at intervals of 120° and a camera facing the non-magnetic frame 4 may be provided so that the position variation of the helmet can be measured by using the camera. This measurement result can be used at the time of MRI measurement. For example, the control device 5 can calibrate the MR image by calculating the relative position between the gradient magnetic field coil 8 and the receive coil 22 using the measurement result. As a result, a high-resolution MR image can be acquired even if the head of the subject moves. This is a useful configuration for MRI measurement of a subject whose head is difficult to fix, such as an infant. In addition, at the time of brain's magnetic field measurement, even if the position of the head is displaced, the magnetic field at the position of the optically pumped magnetometer 1A in the displaced state is canceled so as to be zero. Therefore, the need to measure the position of the non-magnetic frame 4 is low, but the position information of the non-magnetic frame 4 may be used to generate a zero magnetic field.

In addition, in the brain measurement apparatus M1 of the embodiment described above, the magnetic shield 25 is not always necessary. When the magnetic shield 25 is omitted, a coil capable of applying a magnetic field in the opposite direction in order to cancel the static magnetic field on the optically pumped magnetometer 23A may be provided in the OPM module 23.

In the embodiment described above, it is preferable that the static magnetic field nulling coil includes coil systems, which are arranged so as to be perpendicular to each other and surround each of the multiple optically pumped magnetometers and which can apply magnetic fields in three directions perpendicular to each other, for each of the multiple optically pumped magnetometers and that the controller determines a current for the coil systems so that the magnetic field at the position of each of the multiple optically pumped magnetometers approaches zero. According to such a configuration, the coil system is arranged for each of the multiple optically pumped magnetometers so as to correspond to the components in the three directions (x axis, y axis, and z axis) of the static magnetic field. Then, by controlling the current for each of the coil systems, a magnetic field that cancels each of the x-axis direction component, the y-axis direction component, and the z-axis direction component of the static magnetic field is generated for each of the multiple optically pumped magnetometers, and the static magnetic field is canceled in the three directions. Therefore, since the current can be finely controlled for each of the multiple optically pumped magnetometers, the cancellation accuracy of the static magnetic field is improved. In addition, since only the static magnetic field of a region relevant to the operation of the multiple optically pumped magnetometers is canceled, it is possible to suppress an increase in power consumption due to unnecessary cancellation. In addition, the static magnetic field nulling coil can also cancel the gradient of the environmental magnetic field for each of the multiple optically pumped magnetometers.

In addition, it is also preferable that the magnetoencephalograph further includes multiple magnetic sensors for active shield for measuring the fluctuating magnetic field at the position of each of the multiple optically pumped magnetometers and an active shield coil for canceling the fluctuating magnetic field and that, when measuring the brain's magnetic field, the controller controls a current to be supplied to the active shield coil based on the measured values of the multiple magnetic sensors for active shield and determines a current to be supplied to the active shield coil so as to generate a magnetic field for canceling the fluctuating magnetic field at the position of each of the multiple optically pumped magnetometers. According to such a configuration, since the fluctuating magnetic field at the positions of the multiple optically pumped magnetometers is canceled, the multiple optically pumped magnetometers can measure the brain's magnetic field in a state in which the influence of the fluctuating magnetic field is reliably avoided. As a result, the brain's magnetic field can be measured with high accuracy without using the magnetic shield room.

In addition, it is also preferable that the active shield coil is a pair of coils arranged with multiple optically pumped magnetometers interposed therebetween. According to such a configuration, the fluctuating magnetic field at the positions of the multiple optically pumped magnetometers interposed between the pair of active shield coils is effectively canceled. In this manner, the fluctuating magnetic field can be appropriately canceled by a simple configuration.

In addition, it is also preferable to further include an output coil, which is electrically connected to the receive coil and is configured to output a magnetic signal based on the current flowing through the receive coil, and another optically pumped magnetometer configured to detect the magnetic signal output by the output coil, and it is preferable that the controller generates an MR image based on the magnetic signal detected by another optically pumped magnetometer. According to such a configuration, since the signal can be received by another optically pumped magnetometer having a high sensitivity of fT or more, the accuracy of MR image measurement can be improved. In addition, since another optically pumped magnetometer is arranged at a position away from the receive coil to which a static magnetic field of approximately mT is applied, it is possible to adjust the sensitivity band of the sensor without being affected by the static magnetic field.

In addition, it is also preferable that the multiple optically pumped magnetometers are axial gradiometers having a measurement region and a reference region in a direction perpendicular to the scalp of the subject and coaxially.

According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

In addition, it is also preferable that the multiple optically pumped magnetometers, the multiple magnetic sensors for static magnetic field cancellation, and the receive coil are fixed to the helmet-type non-magnetic frame attached to the head of the subject. According to such a configuration, the non-magnetic frame attached to the head and each sensor and the receive coil fixed to the non-magnetic frame move according to the movement of the head of the subject. Therefore, even when the head of the subject moves, it is possible to appropriately cancel the static magnetic field at the positions of the multiple optically pumped magnetometers, measure the brain's magnetic field, and perform MRI measurement. As a result, it is possible to suppress registration errors in both measurements.

In addition, an electromagnetic shield for shielding high-frequency electromagnetic noise may be further provided. According to such a configuration, it is possible to prevent high-frequency electromagnetic noise, which is not a measurement target of the magnetoencephalograph, from entering the multiple optically pumped magnetometers. As a result, the measurement of the brain's magnetic field by the multiple optically pumped magnetometers can be stably performed. On the other hand, in the MRI measurement, it is possible to prevent the intrusion of noise in the 20 kHz to 500 kHz band, which is a signal region.

In addition, it is also preferable that the static magnetic field nulling coil is configured to apply the bias magnetic field to the multiple optically pumped magnetometers so as to be sensitive to frequencies included in the range of 0 to 200 Hz. With such a configuration, the measurement sensitivity of the brain's magnetic field can be increased.

In addition, it is also preferable that another optically pumped magnetometer is configured to be applied the bias magnetic field so as to be sensitive to frequencies included in the range of 20 kHz to 500 kHz. In this case, the accuracy of MRI measurement can also be improved.

What is claimed is:

1. A brain measurement apparatus, comprising:
    a magnetoencephalograph including multiple optically pumped magnetometers configured to measure a brain's magnetic field, multiple magnetic sensors for static magnetic field cancellation configured to measure a static magnetic field at a position of each of the multiple optically pumped magnetometers, and a static magnetic field nulling coil for canceling the static magnetic field;
    an MRI apparatus including a permanent magnet for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse; and
    a controller configured to, when measuring the brain's magnetic field, control a current to be supplied to the static magnetic field nulling coil based on measured values of the multiple magnetic sensors for static magnetic field cancellation and operate so as to cancel a static geomagnetic field and a static magnetic field generated by the permanent magnet at the position of each of the multiple optically pumped magnetometers and, when measuring an MR image, control the gradient magnetic field by controlling a current to be supplied to the gradient magnetic field coil and generate an MR image based on an output of the receive coil.

2. The brain measurement apparatus according to claim 1, wherein the static magnetic field nulling coil includes coil systems, which are arranged so as to be perpendicular to each other and surround each of the multiple optically pumped magnetometers and which are able to apply magnetic fields in three directions perpendicular to each other, for each of the multiple optically pumped magnetometers, and
    the controller determines a current for the coil systems so that a magnetic field at the position of each of the multiple optically pumped magnetometers approaches zero.

3. The brain measurement apparatus according to claim 1, wherein the magnetoencephalograph further includes:
    multiple magnetic sensors for active shield configured to measure a fluctuating magnetic field at the position of each of the multiple optically pumped magnetometers; and
    an active shield coil for canceling the fluctuating magnetic field, and
    when measuring the brain's magnetic field, the controller controls a current to be supplied to the active shield coil based on measured values of the multiple magnetic sensors for active shield and determines a current to be supplied to the active shield coil so as to generate a magnetic field that cancels the fluctuating magnetic field at the position of each of the multiple optically pumped magnetometers.

4. The brain measurement apparatus according to claim 3, wherein the active shield coil is a pair of coils arranged with the multiple optically pumped magnetometers interposed therebetween.

5. The brain measurement apparatus according to claim 1, further comprising:
    an output coil that is electrically connected to the receive coil and is configured to output a magnetic signal based on a current flowing through the receive coil; and
    another optically pumped magnetometer configured to detect the magnetic signal output by the output coil,
    wherein the controller generates the MR image based on the magnetic signal detected by the another optically pumped magnetometer.

6. The brain measurement apparatus according to claim 5, wherein the another optically pumped magnetometer is configured to be applied a bias magnetic field so as to be sensitive to frequencies included in a range of 20 kHz to 500 kHz.

7. The brain measurement apparatus according to claim 1, wherein the multiple optically pumped magnetometers are axial gradiometers having a measurement region and a reference region in a direction perpendicular to a measurement location and coaxially.

8. The brain measurement apparatus according to claim 1, wherein the multiple optically pumped magnetometers, the multiple magnetic sensors for static magnetic field cancellation, and the receive coil are fixed to a non-magnetic frame above a measurement location.

9. The brain measurement apparatus according to claim 1, further comprising:
    an electromagnetic shield for shielding high-frequency electromagnetic noise.

10. The brain measurement apparatus according to claim 1,
wherein the static magnetic field nulling coil is configured to apply a bias magnetic field to the multiple optically pumped magnetometers so as to be sensitive to frequencies included in a range of 0 to 200 Hz.

11. A brain measurement method using a magnetoencephalograph including multiple optically pumped magnetometers configured to measure a brain's magnetic field, multiple magnetic sensors for static magnetic field cancellation configured to measure a static magnetic field at a position of each of the multiple optically pumped magnetometers, and a static magnetic field nulling coil for canceling the static magnetic field and an MRI apparatus including a permanent magnet for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse, the method comprising:

when measuring the brain's magnetic field, controlling a current to be supplied to the static magnetic field nulling coil based on measured values of the multiple magnetic sensors for static magnetic field cancellation and operating so as to cancel a static geomagnetic field and a static magnetic field generated by the permanent magnet at the position of each of the multiple optically pumped magnetometers; and when measuring an MR image, controlling the gradient magnetic field by controlling a current to be supplied to the gradient magnetic field coil and generating an MR image based on an output of the receive coil.

12. The brain measurement method according to claim 11,
wherein the static magnetic field nulling coil includes coil systems, which are arranged so as to be perpendicular to each other and surround each of the multiple optically pumped magnetometers and which are able to apply magnetic fields in three directions perpendicular to each other, for each of the multiple optically pumped magnetometers, and
a current for the coil systems is determined so that a magnetic field at the position of each of the multiple optically pumped magnetometers approaches zero.

* * * * *